Sept. 5, 1961 | W. FLEMER III | Plant Pat. 2,087
LINDEN TREE
Filed Nov. 7, 1960 | 2 Sheets-Sheet 1
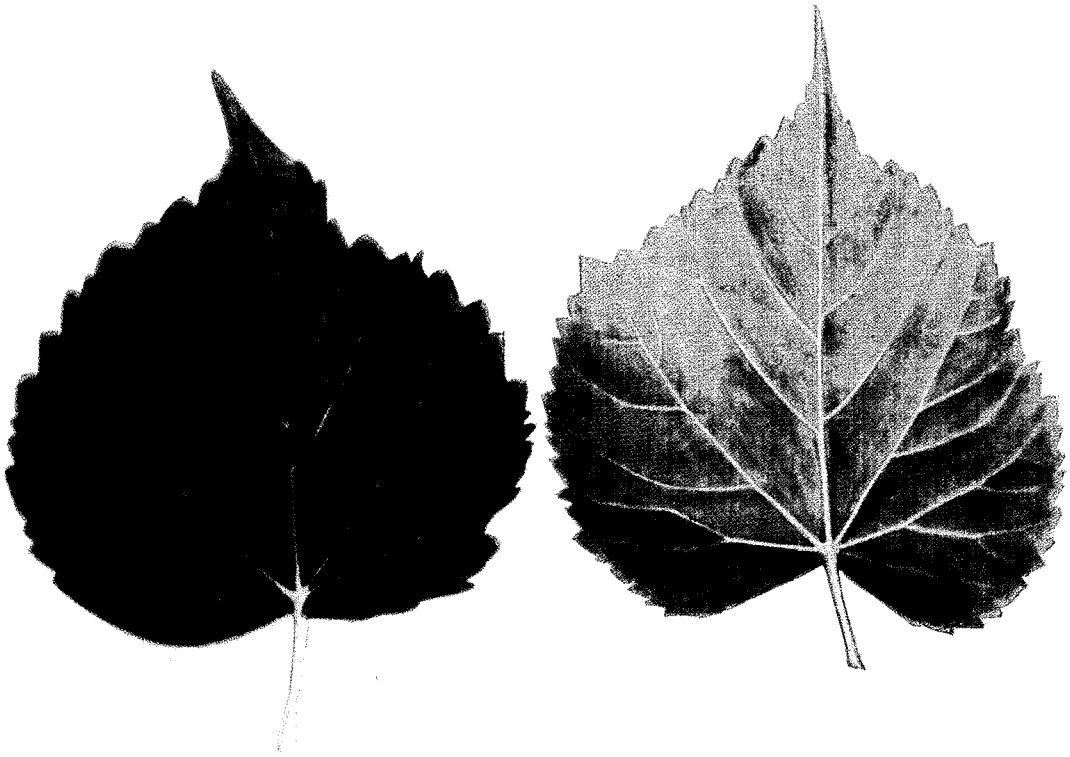
Inventor
William Flemer III
By: Robb & Robb
Attorneys.

Sept. 5, 1961 W. FLEMER III Plant Pat. 2,087
LINDEN TREE
Filed Nov. 7, 1960 2 Sheets-Sheet 2
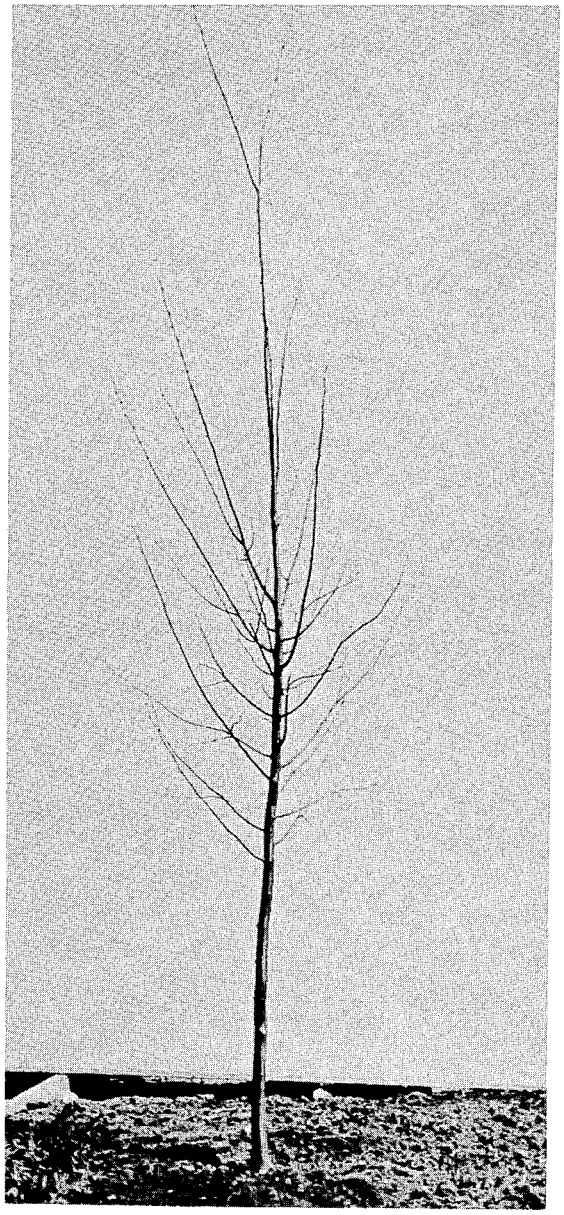
INVENTOR
William Flemer III
BY Robb & Robb
ATTORNEYS United States Patent Office Plant Pat. 2,087
Patented Sept. 5, 1961

2,087
LINDEN TREE

William Flemer III, Princeton, N.J., assignor to Princeton Nurserymen's Research Associates, Princeton, N.J., a partnership Filed Nov. 7, 1960, Ser. No. 67,868
1 Claim. (Cl. 47—59)

The present invention relates to a new and distinct variety of *Tilia europaea* (commonly known as Linden tree), which was originated by me as a selected seedling that was bred from crossing the variety of *Tilia cordata* named "Euclid" (unpatented) with the variety of *Tilia platyphyllos* identified as #541 (unpatented), the former being the male parent and the latter being the female parent.

As the result of this breeding, I have produced a new and improved variety of Linden tree which is endowed with the following outstanding characteristics which distinguish the new variety from its parents, as well as from all other varieties of which I am aware:

(1) A straight trunk which needs no costly staking operations;

(2) Lustrous dark blue-green foliage which is retained even during dry periods.

(3) A handsome and unusually regular, narrow-upright head or crown which does not require pruning;

(4) Exceptionally clean foliage even when grown in dusty locations, and good resistance thereof to aphids, with consequent absence of "sooty" appearance attributed to the honeydew which such insects emit; and (5) A moderate rate of growth.

Asexual reproduction of my new Linden tree by budding (sometimes called bud-grafting), as performed by me at my nursery in the township of Plainsboro, in the State of New Jersey, showns that the foregoing characteristics and distinctions come true to form and are established and transmitted through succeeding propagations.

The accompanying drawings show typical specimens of the foliage of my new variety, with one view depicting the upper surface thereof and another view the lower surface thereof, as illustrated in color as nearly true as it is reasonably possible to make the same in a color illustration of this character and, in addition, a typical tree, without foliage and which depicts in black and white the general form and branching habit of the tree.

The following is a detailed description of my new variety, with color terminology in accordance with the Munsell Color Chart, except where general color terms of ordinary dictionary significance are obvious:

Parentage: Seedling.
*Male parent.*—"Euclid."
*Female parent.*—An unnamed *Tilia platyphyllos* identified as #541.

Propagation: Holds its distinguishing characteristics through succeeding propagations by budding.

Locality where grown and observed: Princeton, New Jersey.

Tree: Small size; vigorous; very upright; medium tall; medium slow growing; hardy.
*Head.*—Very dense; narrow ovate form.
*Trunk.*—Medium slender. Bark—smooth.
*Branches.*—Medium slender; dense branching; excurrent pattern. Bark—smooth. Color—olive brown, plate 2.5Y3/2 (value=3, chroma=2).
*Lenticels.*—Abundant; small.

Foliage:
*Leaves.*—Leathery; with exceptionally lustrous and highly glossed upper surface which does not collect dirt and dust; glaucous on lower surface; small size; orbicular; equally cordate; acuminate; sometimes slightly 3-lobed on rapidly growing young shoots; thick; with small axillary tufts of hair. Length along midrib—from 9.0 to 10.5 cm. Width—from 9.0 to 9.5 cm. Margin—coarsely serrate; width between serrations about 5 mm.; depth of serrations about 2 mm. Color (mature): upper surface—Glossy Forest Green, Plate 5.0GY3/4; under surface—Glaucous Grey-Green, Plate 5.0GY5/2. Petiole—short; from 2.0 to 2.5 cm. in length; thick; color—Yellow, Plate 10.0Y5/6.

Flowers: Mid-season, as compared with other varieties; large; from 6 to 8 per cyme; floral bract from 7 to 8 cm. long; fragrant. Color—Pale Yellow-Green, Plate 7.5Y8/8.

Fruit: Not especially productive; 5 or 6 per cyme; about 8 mm. wide; about 7 mm. long; moderately pubescent.

Disease and insect resistance: Average resistance to disease and good resistance to aphids, as determined by comparison with other varieties grown under comparable cultural conditions at Princeton, New Jersey; good resistance to aphids results in absence of "sooty" appearance of foliage attributed to the honeydew which such insects emit.

I claim:

A new and distinct variety of Linden tree (*Tilia europaea*), substantially as herein shown and described, characterized particularly as to novelty by the unique combination of a straight habit of trunk growth, attractive and lustrous dark blue-green foliage and the habit thereof to remain green even in dusty locations, as well as a habit of retaining the dark green color during periods of drought, good resistance of the foliage to aphids, with consequent absence of a "sooty" appearance, a handsome and unusually regular narrow-upright head or crown which does not require pruning to achieve an attractive shape, and a moderate rate of growth.

No references cited.